US009688271B2

(12) United States Patent
Chan et al.

(10) Patent No.: US 9,688,271 B2
(45) Date of Patent: Jun. 27, 2017

(54) OCCUPANT BASED VEHICLE CONTROL

(71) Applicant: Elwha LLC, Bellevue, WA (US)

(72) Inventors: Alistair K. Chan, Bainbridge Island, WA (US); Tom Driscoll, San Diego, CA (US); Roderick A. Hyde, Redmond, WA (US); Jordin T. Kare, San Jose, CA (US); David R. Smith, Durham, NC (US); Clarence T. Tegreene, Mercer Island, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 14/644,995

(22) Filed: Mar. 11, 2015

(65) Prior Publication Data

US 2016/0264131 A1 Sep. 15, 2016

(51) Int. Cl.
*G01C 22/00* (2006.01)
*A61B 5/00* (2006.01)
*H04N 9/47* (2006.01)
*B60W 30/02* (2012.01)
*B60W 40/08* (2012.01)

(52) U.S. Cl.
CPC .......... *B60W 30/025* (2013.01); *B60W 40/08* (2013.01); *B60W 2040/0881* (2013.01); *B60W 2900/00* (2013.01)

(58) Field of Classification Search
USPC ................. 701/23; 600/301; 348/77
See application file for complete search history.

(56) References Cited

U.S. PATENT DOCUMENTS

| 6,906,619 | B2 | 6/2005 | Williams et al. |
| 7,027,621 | B1* | 4/2006 | Prokoski ............ G06K 9/00255 |
| | | | 180/272 |
| 7,415,126 | B2 | 8/2008 | Breed et al. |
| 8,483,909 | B2* | 7/2013 | Visconti ................ B60W 40/09 |
| | | | 180/272 |
| 8,874,301 | B1 | 10/2014 | Rao et al. |
| 2005/0030184 | A1 | 2/2005 | Victor |
| 2006/0235753 | A1 | 10/2006 | Kameyama |

(Continued)

FOREIGN PATENT DOCUMENTS

KR 10-2004-0054253 A 6/2004
KR 10-2012-0128423 A 11/2012

OTHER PUBLICATIONS

Build Empathy: The Stress of Driving in a Google Self-Driving Car, retrieved from BlogSpot.com (http://hedmanresearch.blogspot.com/2011/12/stress-of-driving-in-google-self.html), printed Mar. 16, 2015, 2 pages.

(Continued)

*Primary Examiner* — Tyler Paige
(74) *Attorney, Agent, or Firm* — Foley & Lardner LLP

(57) ABSTRACT

A vehicle includes an occupant monitoring system and a processing circuit coupled to the occupant monitoring system. The occupant monitoring system is configured to acquire occupant data regarding an occupant of the vehicle. The processing circuit is configured to receive the occupant data; determine a vehicle operation command based on the occupant data, the vehicle operation command configured to affect operation of the vehicle while the vehicle is in a robotic driving mode; and provide the vehicle operation command to a vehicle system.

34 Claims, 6 Drawing Sheets

(56) References Cited

U.S. PATENT DOCUMENTS

| | | | |
|---|---|---|---|
| 2014/0104405 A1* | 4/2014 | Weidl | A61B 5/02416 |
| | | | 348/77 |
| 2014/0135598 A1* | 5/2014 | Weidl | A61B 5/6893 |
| | | | 600/301 |
| 2015/0246673 A1* | 9/2015 | Tseng | B60W 30/00 |
| | | | 701/23 |
| 2015/0309512 A1* | 10/2015 | Cudak | G05D 1/0287 |
| | | | 701/23 |
| 2016/0001781 A1* | 1/2016 | Fung | G06F 19/345 |
| | | | 701/36 |

OTHER PUBLICATIONS

PCT International Search Report; International App. No. PCT/US2016/020374; Jun. 10, 2016; pp. 1-3.

* cited by examiner

OCCUPANT BASED VEHICLE CONTROL

BACKGROUND

Automobile technology has steadily progressed over the years. Engines have become more efficient. Potentially harmful exhaust emissions have decreased. Vehicle power output has increased while vehicle weight has decreased. Along with these developments, robotic driving devices are being developed that enable the vehicle to be robotically operated (i.e., a self-driving vehicle). Self-driving vehicles will reduce the importance of operator quality and enable people otherwise prohibited from driving to "operate" the vehicle (e.g., a person who is blind). However, self-driving vehicles may have operating characteristics significantly different from human-operated vehicles, such as in the aspects of handling, braking, and maneuvering in traffic. Thus, particularly during the introduction of self-driving vehicles, some operators of and passengers in such vehicles may find some of the vehicle's actions unexpected, unpleasant, or even frightening.

SUMMARY

One embodiment relates to a vehicle including an occupant monitoring system and a processing circuit coupled to the occupant monitoring system. The occupant monitoring system is configured to acquire occupant data regarding an occupant of the vehicle. The processing circuit is configured to receive the occupant data; determine a vehicle operation command based on the occupant data, wherein the vehicle operation command is configured to affect operation of the vehicle while the vehicle is in a robotic driving mode; and provide the vehicle operation command to a vehicle system. In one embodiment, the vehicle operation command is provided to an operator of the vehicle (e.g., via a display screen or monitor in the vehicle) to choose whether to implement the vehicle operating command with the vehicle.

Another embodiment relates to a vehicle including an occupant monitoring system, a robotic driving system, and a processing circuit coupled to the occupant monitoring system and the robotic driving system. The occupant monitoring system is configured to acquire data regarding an occupant of the vehicle. The robotic driving system is configured to provide robotic control of the vehicle during a robotic driving mode. The processing circuit is configured to receive the occupant data; determine a vehicle operation command based on the occupant data, wherein the vehicle operation command is configured to affect operation of the vehicle while the vehicle is in a robotic driving mode; and provide the vehicle operation command to a vehicle system. According to one embodiment, the vehicle system includes the robotic driving system.

Still another embodiment relates to a vehicle including an occupant monitoring system, a vehicle monitoring system, and a processing circuit coupled to the occupant monitoring system and the vehicle monitoring system. The occupant monitoring system is configured to acquire occupant data regarding an occupant of the vehicle. The vehicle monitoring system is configured to acquire vehicle operation data. The processing circuit is configured to receive the occupant data; receive the vehicle operation data; provide an output to the occupant regarding operation of the vehicle; and provide a vehicle operation command to a robotic driving system of the vehicle based on the occupant data and the vehicle operation data, wherein the vehicle operation command is configured to affect operation of the vehicle while the vehicle is in a robotic driving mode.

Yet another embodiment relates to a vehicle including an occupant monitoring system and a processing circuit coupled to the occupant monitoring system. The occupant monitoring system is configured to acquire occupant data regarding an occupant of the vehicle. The processing circuit is configured to identify an occupant of the vehicle; retrieve an occupant profile for the occupant based on identification of the occupant; receive the occupant data; determine a vehicle operation command based on the occupant data and the occupant profile, wherein the vehicle operation command is configured to affect operation of the vehicle while the vehicle is in a robotic driving mode; and provide the vehicle operation command to a vehicle system.

Still another embodiment relates to a method of operating a robotic driving vehicle, including: receiving, by a processing circuit, occupant data; determining, by the processing circuit, a vehicle operation command based on the occupant data, wherein the vehicle operation command is configured to affect operation of a vehicle while the vehicle is in a robotic driving mode; and providing, by the processing circuit, the vehicle operation command to a vehicle system.

Another embodiment relates to a method of operating a robotic driving vehicle, including: receiving occupant data; receiving vehicle operation data; providing an output to an occupant of a vehicle regarding operation of the vehicle; and providing a vehicle operation command to a robotic driving system of the vehicle based on the occupant data and vehicle operation data, wherein the vehicle operation command is configured to affect operation of the vehicle while the vehicle is in a robotic driving mode.

Yet another embodiment relates to a method of operating a robotic driving vehicle, including: identifying, by a processing circuit, an occupant of a vehicle; receiving, by the processing circuit, occupant data; determining, by the processing circuit, a vehicle operation command based on the occupant data; and providing, by the processing circuit, the vehicle operation command to a vehicle system; wherein the vehicle operation command is configured to affect operation of the vehicle while the vehicle is in a robotic driving mode.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
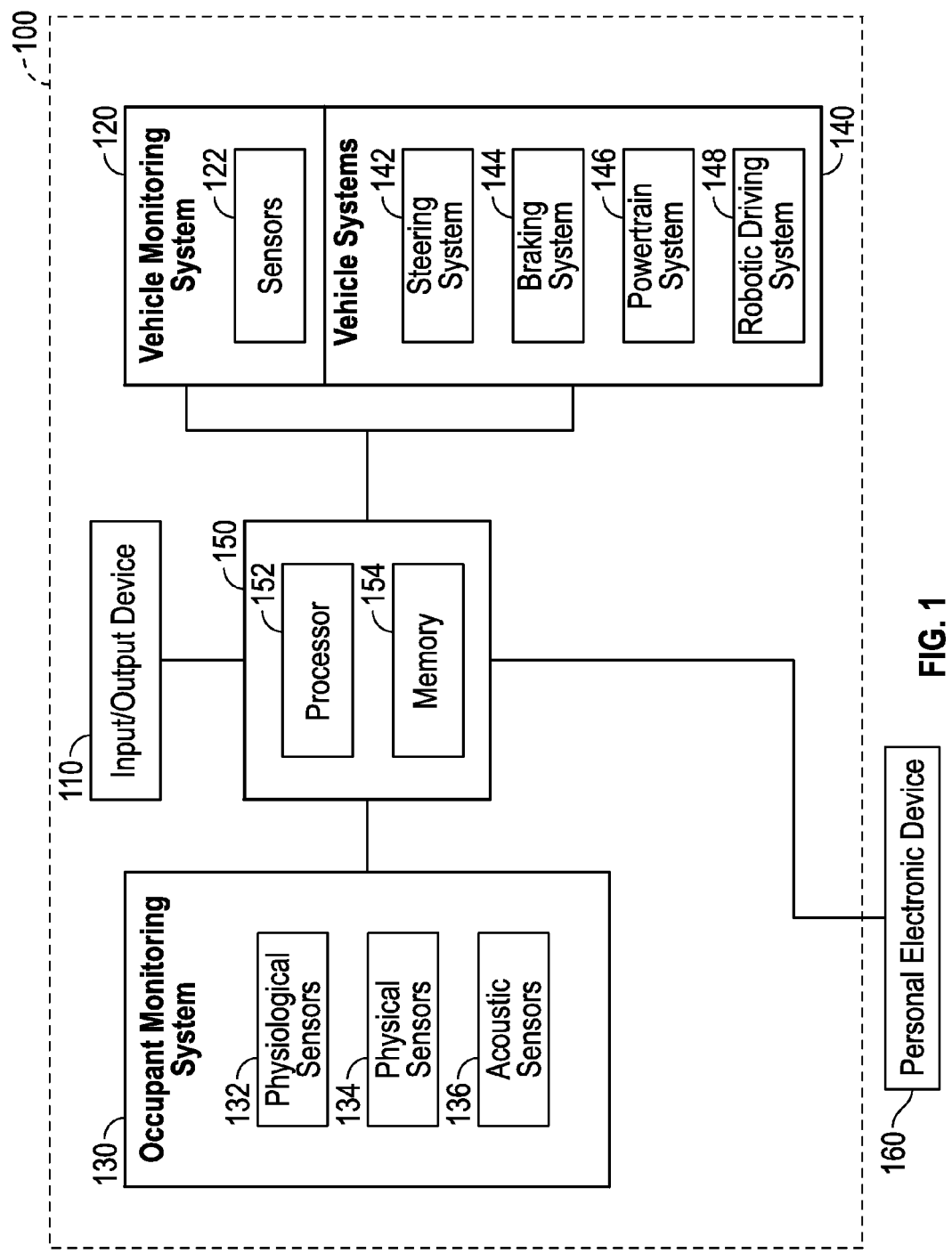
FIG. 1 is a diagram of an occupant monitoring system coupled to a processing circuit in a vehicle, according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, various embodiments disclosed herein relate to systems and methods of controlling a robotic driving vehicle based on the non-deliberate reactions of one or more occupants. These non-deliberate reactions may indicate a presence of discomfort, stress, or other mental and/or physical state(s) regarding one or more of the occupants of the vehicle who may be affected by operation of the vehicle. Until recently, all road vehicles were controlled directly by a human operator (the driver). As a result, both drivers and passengers were and are accustomed to the behavior of human-controlled vehicles. For example, even when a passenger is riding with an unfamiliar driver (e.g., one who drives more or less aggressively than the passenger is used to) who may cause passenger reactions such as fear or frustration, the passenger still has a level of familiarization with the human-controlled vehicle. To that end, passengers may also react in various ways to various vehicle events, for example being upset by a near-collision or a sudden bump. A human operator may sense and respond to both verbal input and nonverbal cues from passengers, and adjust his or her driving style as appropriate. Today, sophisticated sensing and computer control systems are being developed that enable automobiles to be robotically operated (i.e., self-driving). As mentioned above, self-driving vehicles will reduce the importance of operator quality and enable people otherwise prohibited from driving to "operate" the vehicle (e.g., a person who is blind). However, particularly during the introduction of self-driving vehicles, some operators of and passengers in such vehicles may find some of the vehicle's actions unexpected, unpleasant, or even frightening. As such, various embodiments disclosed herein relate to enabling a self-driving vehicle to monitor and respond to the reactions of some or all of the occupants of the vehicle.

The robotic driving vehicle may be operable in two modes: a manual driving mode and a robotic driving mode. Manual driving mode refers to driver-controlled vehicle operation and robotic driving mode refers to autonomous vehicle operation (i.e., a self-driving vehicle). While in robotic driving mode, an occupant monitoring system acquires data regarding the physical and/or emotional state of one or more of the occupants of the vehicle. This data is hereinafter referred to as "occupant data." The occupant data may be acquired explicitly and/or implicitly, where explicitly refers to the occupant directly providing the data and implicitly refers to one or more sensors detecting and acquiring the data. The occupant data provides an indication of discomfort or another condition for one or more occupants. As the vehicle is being operated autonomously, occupants of the vehicle may feel uneasy, lacking control, unfamiliar with robotic driving vehicles, and/or in a general state of discomfort. A processing circuit uses the occupant data to determine that one or more occupants are uncomfortable. Based on this determination, the processing circuit provides a command to one or more systems of the vehicle, where the command is structured to control an operating parameter of the vehicle. For example, while in robotic driving mode, the vehicle may have a preset maximum following distance of ten feet. While the vehicle is maintaining this distance, the occupant monitoring system is acquiring data that indicates the heart rate of an occupant of the vehicle has increased above a threshold value (e.g., due to the discomfort that the occupant is feeling while the vehicle is self-driving). The processing circuit determines this increase may be attributed to the vehicle following distance. As a result, the processing circuit provides a vehicle operation command to increase the following distance to twenty-five feet. These operations may be continuously performed until an occupant specifies a distance, the heart rate has decreased (i.e., there is no longer an indication of discomfort), or the vehicle is placed into manual driving mode. Thus, the processing circuit, in conjunction with the occupant monitoring system, operates to relieve discomfort from the occupants of a self-driving vehicle.

According to another embodiment, the state of discomfort may also include an indication of boredom, irritation, or the like that indicates that the self-driving vehicle is operating too conservatively for one or more of the occupants. For example, the processing circuit may receive occupant data of a passenger repeatedly tapping a floor of the vehicle. The processing circuit may determine that the passenger is irritated and provide a command to increase, for example, the vehicle speed. In this configuration, the processing circuit is structured to relieve stress/discomfort due to conservative operation of the vehicle while in robotic driving mode.

In some embodiments, the processing circuit also receives vehicle operation data that provides an indication of the current operating parameters of the vehicle (e.g., vehicle speed, a following distance, etc.). Using the occupant data, the processing circuit determines one or more output correlations between the vehicle operating parameters and the occupant data (e.g., at "X" vehicle speed, the stress level is at "Y"). These correlations may be provided to the occupants of the vehicle and/or used to optimize one or more vehicle operating parameters. In certain embodiments, an occupant or user may specify vehicle commands for certain occupant data points, indicate occupant data points that show discomfort, provide responses (e.g., a vehicle operation command) based on the occupant data, and/or otherwise customize the system to selected preferences.

Further, the occupant monitoring system may be configured to recognize certain occupants as having different privileges. In this regard, the processing circuit may be configured to selectively control/adjust an operating parameter of the vehicle differently based on each occupant. For example, one occupant (e.g., the one seated proximate to the manual driving controls (e.g., transmission shifter, steering wheel, pedals, etc.)) may be considered the vehicle operator and, therefore, given priority, or sole authority in specifying one or more driving characteristics of the robotic driving vehicle. While a passenger of the vehicle may desire to increase the following distance of the vehicle, the operator may have a predefined following distance that prohibits the passenger from increasing the following distance. In another embodiment, the operator may provide an input that overrides the desire of the passenger. Accordingly, the privileges of certain occupants may differ based on the type of occupant (e.g., an owner, an operator, a passenger, etc.), such that, as described more fully herein, the processing circuit may respond differently based on occupant data for various types of occupant. These and other features of the present disclosure are described more fully herein.

Referring now to FIG. 1, occupant monitoring system 130 coupled to processing circuit 150 in vehicle 100 is shown, according to one embodiment. Processing circuit 150 is communicably coupled to input/output (I/O) device 110, vehicle monitoring system 120, vehicle systems 140, and personal electronic device 160. As occupant monitoring system 130 and processing circuit 150 may be implemented in a wide range of vehicles, vehicle 100 may include, but is not limited to, sedan automobiles, two- and three-wheeled motorbikes, sport-utility-vehicles, station wagons, vans, trucks, semi-tractor trailers, hybrid vehicles, full electric vehicles, aircraft, watercraft, etc. Accordingly, vehicle systems 140 are not limited to those depicted in FIG. 1, but may also include application-specific systems (e.g., a battery management system for a full electric vehicle).

Communications between and among the components of FIG. 1 may be via any data protocol, using any wired or wireless transmission medium. For example, a wired system may employ analog signals, a serial data protocol (RS-232, RS-442), an Ethernet protocol, a Universal Serial Bus (USB) protocol, etc., that is transmitted over twisted pair cables, coaxial cables, fiber optic cables, etc. A wireless system may employ any of these protocols, or a wireless-only protocol such as Bluetooth or Wi-Fi (various versions of 802.11), transmitted via radio (RF), e.g., at 2.4 GHz or 5 GHz, optical or infrared beams, ultrasonic signals, or electromagnetic induction. In one embodiment, the Controller Area Network (CAN) bus protocol may be used to exchange digital data over a wired or wireless bus.

Personal electronic device 160 may include any type of electronic device that an occupant of vehicle 100 may carry. For example, personal electronic device 160 may include, but is not limited to, a mobile phone, a watch, a personal digital assistant (PDA), a laptop computer, a tablet computer, any other computing device, an electronic bracelet or necklace, etc.

Vehicle systems 140 may include steering system 142, braking system 144, powertrain system 146, and robotic driving system 148. Robotic driving system 148 is configured to autonomously operate vehicle 100 (i.e., robotic driving mode). Steering system 142 refers to the components and control systems that enable directional control of the vehicle. Braking system 144 refers to the components and control systems for the brakes of vehicle 100. Powertrain system 146 refers to the propulsion components and control systems of vehicle 100. Powertrain system 146 may include an engine, a transmission, a drive/propeller shaft, a differential, and a final drive (e.g., the wheels of vehicle 100). Because vehicle 100 is widely variable (e.g., full electric to a solely internal combustion engine driven vehicle), the components of powertrain system 146 (and vehicle 100, in general) may also be widely variable. For example, the engine may include a spark-ignition engine or a compression-ignition engine. The transmission may include an automatic transmission, a manual transmission, a dual clutch transmission, etc. Additionally, vehicle systems 140 may include auxiliary systems such as a heating and air conditioning system, an exhaust treating system, or a positioning system. Accordingly, as described herein, when processing circuit 150 provides a vehicle operation command to a vehicle system, the command is structured to control one or more systems (and components within the system) to affect a desired operating parameter. For example, processing circuit 150 may command the transmission to downshift in order to slow the vehicle speed and increase a following distance.

Vehicle monitoring system 120 is structured to acquire vehicle operation data from one or more vehicle systems 140. Vehicle monitoring system 120 may include one or more vehicle monitoring sensors 122 that are coupled to vehicle systems 140. Sensors 122 may be located within vehicle 100 or external of vehicle 100 (e.g., on the outside of vehicle 100). Sensors 122 acquire the vehicle operation data and transmit the acquired data to processing circuit 150. Sensors 122 may include a vehicle speed sensor; an accelerometer; an inclinometer; a vehicle load sensor; radar systems (e.g., lidar, laser, etc.) that detect objects near the vehicle; temperature sensors; pressure sensors; etc. In some embodiments, the vehicle operation data provides an indication of current vehicle operating parameters. In other embodiments, the vehicle operation data is used by processing circuit 150 to determine one or more vehicle operating parameters. The vehicle operation data may be acquired periodically or continuously and may be acquired in robotic driving mode, manual driving mode, or both. The vehicle operation data may include, but is not limited to: a vehicle speed; an engine speed; a separation distance to other vehicles; a vehicle load; a current gear/setting of a transmission; etc.

As mentioned above, the vehicle operation data provides an indication of one or more vehicle operating parameters, which may be determined by processing circuit 150. In one embodiment, the vehicle operating parameters correspond with the operating characteristics of vehicle 100 in robotic driving mode. Accordingly, the vehicle operating parameters may include, but are not limited to: a current vehicle driving mode (e.g., robotic or manual); a vehicle speed relative to another vehicle, or other traffic in general; an absolute vehicle speed; a following distance; an acceleration characteristic (e.g., a time to accelerate to X miles-per-hour); a braking characteristic (e.g., a stopping distance); a vehicle turning characteristic (e.g., the vehicle may make sharp turns as opposed to gradual turns); a separation distance relative to other vehicles and/or objects; etc. As described herein, processing circuit 150 provides vehicle operation commands structured to adjust one or more vehicle operating parameters in order to decrease occupant discomfort while in robotic driving mode.

As the components of FIG. 1 are shown to be embodied in vehicle 100, processing circuit 150 may be structured as an electronic control module (ECM). The ECM may include a transmission control unit, an engine control unit, and any other control unit included in a vehicle (e.g., a powertrain control module, etc.). According to one embodiment, processing circuit 150 may be implemented within robotic driving system 148 (e.g., a controller or control system for robotic driving system 148 may include processing circuit 150). In still another embodiment, processing circuit 150 may be implemented with an electronic processing system that implements the robotic driving mode for robotic driving system 148. In yet another embodiment, vehicle monitoring system 120 may not be coupled directly to processing circuit 150; vehicle monitoring system 120 may be communicably coupled to robotic driving system 148, and processing circuit 150 may query robotic driving system 148 to obtain raw or processed data regarding the vehicle state that is indicative from the vehicle operation data. All such variations are intended to fall within the spirit and scope of the present disclosure. As shown in FIG. 1, processing circuit 150 includes processor 152 and memory device 154. In some embodiments, the functions of processing circuit 150 described herein are performed by instructions (e.g., software) on machine-readable media and utilize various hardware components. Processor 152 may be implemented as a general-purpose processor, an application specific integrated circuit (ASIC), one or more field programmable gate arrays (FPGAs), a digital-signal-processor (DSP), a group of processing components, or other suitable electronic processing components. Memory device 154 may be configured as one or more memory devices, which are configured to store various pieces of vehicle operation data, selected vehicle operating parameters, occupant profiles, occupant data, and other data. Memory device 154 may be or include non-transient volatile memory or non-volatile memory. Memory device 154 may include database components, object code components, script components, or any other type of information structure for supporting the various activities and information structures described herein. Memory device 154 may be communicably connected to processor 152 (and the other components of vehicle 100) and provide computer code or instructions for executing the processes described herein.

Processing circuit 150 is configured to receive occupant data from occupant monitoring system 130. Occupant monitoring system 130 acquires data regarding one or more occupants of vehicle 100 and transmits the data to processing circuit 150. In one embodiment, the occupant data is continuously acquired when vehicle 100 is turned on (i.e., in manual driving mode and robotic driving mode). In other embodiments, the occupant data is acquired periodically and/or only during robotic driving mode.

As shown, occupant monitoring system 130 include physiological response sensors 132, physical response sensors 134, and acoustic sensors 136 that acquire the occupant data. The occupant data may be acquired both explicitly and implicitly. Implicit data acquisition refers to data acquired by one or more sensors and analyzed by processing circuit 150. Explicit data acquisition refers to data directly provided by one or more occupants. For example, via input/output device 110, an occupant may specify that he/she does not like close following distances. In another example, in response to a sharp turn taken by vehicle 100 during robotic driving mode, an occupant may state, "please do not turn corners that sharply in the future." Processing circuit 150 utilizes that statement to provide one or more vehicle operation commands structured to increase the turning radius for vehicle 100 (i.e., decrease the sharpness).

As mentioned above, physiological response sensors 132, physical response sensors 134, and acoustic sensors 136 acquire the occupant data. Sensors 132, 134, and 136 may be contact (e.g., via handholds) or non-contact. Physical response sensors 134 may detect a physical force or motion (e.g., pushing feet against floor of vehicle 100, grip pressure, etc.). Acoustic sensors 136 may detect voluntary (e.g., "slow down, please") and involuntary sounds (e.g., sudden intake of breath, screams, etc.). Physiological sensors 132 may detect an occupant's response to various vehicle operating maneuvers (e.g., the eye motion, the amount of shaking, and other occupant data points described above). In this example embodiment, the sensors are only shown to include sensors 132, 134, and 136. However, many other types of sensors may also be implemented with occupant monitoring system 130. Thus, the sensors of occupant monitoring system 130 may include cameras, body position sensors, force or pressure sensors, microphones, heart rate/pulse sensors, moisture sensors (e.g., for sweat detection), temperature sensors, a facial sensor (e.g., to detect frowns or facial features that indicate an occupant is uncomfortable), etc. In another embodiment, the facial sensor may also identify an occupant of vehicle 100 in order to retrieve occupant data (e.g., reference data, which is described below) for that occupant.

As mentioned above, the occupant data provides an indication of discomfort of one or more occupants of vehicle 100 during the robotic driving mode. As used herein, the term "discomfort" is not meant to be limiting, such that "discomfort" may refer to a stress, a sense of uneasiness, a sense of distrust with operation of vehicle 100 in robotic driving mode, a sensed medical condition, and any other term used to describe how one is feeling. "Discomfort" may also refer to feelings that indicate impatience with the robotic driving vehicle. For example, the occupant data may also provide an indication of one or more occupants feeling that the robotic driving vehicle is operating too conservatively. In this case, processing circuit 150 may provide a command to increase a vehicle speed, or any other command to alleviate or attempt to alleviate the impatience feeling. As such, "discomfort" is meant to be broadly interpreted in the spirit and scope of the present disclosure.

The occupant data may include, but is not limited to: an eye motion (e.g., a blink rate, eyes closed for an extended period of time that may indicate that one is too scared to even open them, etc.); a pupil size; a perspiration amount and rate; a temperature; an exertion of force (e.g., grip a handhold, press feet to the floor of the vehicle, etc.); a pulse rate; audible information (e.g., voice, breathing rate, etc.); an amount of shaking or trembling; a facial feature (e.g., a frown); an amount of familiarity with robotic driving vehicles; etc. Based on the occupant data, processing circuit 150 may determine for one or more data points (e.g., perspiration amount, temperature, etc.), an average, a rate of change, a peak level, a standard deviation, etc. based on the acquired and stored data. This determination may be correlated with a particular vehicle operating parameter, such as turning, braking, accelerating, etc. (e.g., the average pulse rate for a following distance of X feet is Z pulses per minute).

Processing circuit 150 may utilize one or more predefined standards or preferences provided by the occupants to determine if there is discomfort. The determination may be based on only one occupant, on some of the occupants, or on all the occupants. Processing circuit 150 may determine which vehicle operation command to provide based on one or more occupant data points being outside a predefined standard. The predefined standard may include an acceptable range, a threshold level, and the like. The acceptable range may refer to a range where an occupant data point is determined to not indicate a level of discomfort, such that occupant data points outside that range indicate discomfort. The threshold level may refer to a minimum or maximum value of an occupant data point. These predefined standards may be set via input/output device 110.

For example, a heart rate above ninety beats-per-minute may indicate discomfort. Eyes open for more than forty-five seconds at a time may indicate discomfort. Verbal distress signals (e.g., "I do not like not having control of the vehicle") may indicate discomfort. As mentioned above, defining what occupant data levels indicate discomfort may be done via input/out device 110. As this may be highly customizable, only a few examples were provided above.

Based on the occupant data, processing circuit 150 provides a vehicle operation command that affects one or more vehicle operating parameters while vehicle 100 is in robotic driving mode. The vehicle operation commands may be provided to vehicle systems 140. The vehicle operation commands may include, but are not limited to: an increase to vehicle speed; a decrease to vehicle speed; an increase in following distance; a decrease in following distance; a lateral separation distance adjustment; an adjustment to an acceleration characteristic; an adjustment to a braking characteristic; an adjustment to a turning characteristic; and a deactivation of robotic driving mode. Processing circuit 150 may also provide auxiliary functions, such as increasing or decreasing a cabin temperature, and other functions that are not related to the vehicle driving characteristics. The following paragraphs illustrate examples of how processing circuit 150 determines which vehicle operation command to provide.

Processing circuit 150 may determine which vehicle operation command to provide based on a gradation level of one or more occupant data points from a predefined acceptable range. For example, if the pressure on the floor of vehicle 100 increases by ten percent during robotic driving mode relative to that received in manual driving mode (e.g., the occupant becomes uncomfortable and exerts additional pressure on the floor and their seat in order to achieve a sense of steadiness), processing circuit 150 may not provide any vehicle operation command. However, if the floor pressure increases by fifty percent, processing circuit 150 may completely deactivate robotic driving mode.

Processing circuit 150 may determine which vehicle operation command to provide based on a plurality of occupant data points, as opposed to just a sole occupant data point. While an individual occupant data point may indicate an occupant's discomfort or comfort, processing circuit 150 may utilize a plurality of occupant data points to improve accuracy. For example, when the temperature rises by five degrees Fahrenheit, processing circuit 150 asks the occupants of vehicle 100 if everything is okay. However, if the temperature rises by five degrees Fahrenheit and the moisture content has increased by five percent (which may indicate an increase in perspiration); processing circuit 150 lowers the vehicle speed and turns on the air conditioning system. Thus, the combination of occupant data points led processing circuit 150 to determine there is discomfort, which impacted the vehicle operation command determination.

Processing circuit 150 may also determine which vehicle operation command to provide based on a specific occupant, rather than the occupants as a whole. For example, during robotic driving mode, the occupant data points may indicate an acceptable deviation amount relative to their pre-robotic driving mode occupant data points. However, one occupant has increased their shaking/trembling beyond an acceptable deviation range relative to their shaking/trembling during manual driving mode. Thus, processing circuit 150 may ask the individual if he/she is comfortable and base the vehicle operation command on their response. As such, although the other occupants appear to be comfortable and not stressed, processing circuit 150 functions to accommodate the uncomfortable or likely uncomfortable occupant.

In one embodiment, processing circuit 150 is structured to provide different vehicle operation commands based on a type of occupant in vehicle 100. The occupant type may include, but is not limited to, a passenger, a driver, and an owner. A passenger refers to a rider in the vehicle who may control certain vehicle features, such as an entertainment system and a heating/air conditioning system and not others (e.g., driving controls, such as the brake pedal). A driver refers to an occupant that drives the vehicle in manual driving mode. When in robotic driving mode, the driver may be classified as an operator. An owner refers to an owner of the vehicle (e.g., a person or persons that have a deed of title for the vehicle). Classification of occupant types may be via input/output device 110. It should be understood that the aforementioned categories or classification types is for example purposes only, such that many other categorization/classification systems exists. All such variations are intended to fall within the scope of the present disclosure. For example, a generic classification system may be occupant type 1, occupant type 2, and occupant type 3. Occupant type 1 is provided the most privileges (described below). Occupant type 2 is provided the second-most privileges and occupant type 3 is provided the least-amount of privileges. In other words, processing circuit 150 is structured to be more responsive to the occupant data of occupant type 1, than of occupant type 2, which processing circuit 150 is more responsive to than occupant type 3 (responsiveness indicates the level of weight or consideration given by processing circuit 150 based on the occupant data for the specific occupant type).

Based on the occupant type, processing circuit 150 may provide different vehicle operation commands. The provided vehicle operation commands may correspond with a level of control or privilege given to the occupant based on the categorization or classification of the occupant. For example, an "owner" may be allowed to change or lock parameters that cannot be overridden by any occupant (e.g., a passenger may desire to increase a following distance of the vehicle, but due to a "lock" (e.g., a locked setting, etc.) by the owner, the following distance cannot be increased by more than X feet, such that processing circuit 150 is limited by the extent with which the following distance may be increased). In another example, an owner or other high classified occupant may have additional privileges, such as overriding passenger inputs, (e.g., "ignore passenger A; passenger A gets scared any time the vehicle is operated over 20 miles-per-hour", or "passenger B is our guest; pay extra attention to passenger B", etc.). Processing circuit 150 may use a weighting process or system to provide relatively greater weight to determinations (based on occupant data) and/or inputs from higher classified/categorized occupants. For example, based on the occupant data, processing circuit 150 may determine that an "owner" (in this example, the owner has the highest classification) is not comfortable with current operation of the vehicle but a "passenger" (lowest classification in this example) is comfortable with the current operation. Processing circuit 150 may weight (e.g., give more consideration towards, etc.) the owner's feeling of discomfort more heavily than the passenger's feeling of comfort. Accordingly, processing circuit 150 may provide a vehicle operation command based mainly on the discomfort of the owner to alleviate stress in the robotic driving vehicle of the owner.

Accordingly, in some embodiments, processing circuit 150 may identify an occupant type. Identification may be via an input (e.g., via input/output device 110) and include the same or similar processes described herein. Based on the identification, processing circuit 150 may classify or categorize the occupant. Processing circuit 150 may then interpret occupant data different for each occupant classification, such that processing circuit 150 provides different vehicle operation commands based on the occupant type.

Processing circuit 150 may also determine which vehicle operation command to provide based on a comparison of one or more occupant data points to one or more reference occupant data points. The reference occupant data may represent an average, a trend, a median, and/or a normal operating range of one or more occupant data points. The reference occupant data may be based on a specific occupant; based on all the occupant data acquired for all the occupants of vehicle 100 over one or more vehicle trips; based on occupant data acquired for one or more vehicle 100 occupants during a manual driving mode of vehicle 100; based on occupant data acquired after a predetermined time of operation of vehicle 100; etc.

Reference occupant data may be accumulated/assembled in at least the following four ways. Each of these methods may be classified as data collection modes for reference occupant data. First, as described above, vehicle 100 may operate for a predetermined amount of time (e.g., 15 minutes) in order to gain representative occupant data for use as reference occupant data for a particular occupant. Second, manual driving mode may be used as data collection mode. For example, the driver may be comfortable with how he/she drives the vehicle. Accordingly, occupant data acquired during this time period for the driver may be used as the reference occupant data during a robotic driving mode session. Third, via memory device 154, reference occupant data may be stored for repeat vehicle occupants to prevent a data collection mode for that occupant. And, fourth, processing circuit 150 may be preprogrammed with reference occupant data (e.g., based on one or more standards, conditions, inputs, settings, etc.) to also prevent a data collection mode. In some embodiments, more than one of the aforementioned methods may be collectively used. All such variations are intended to fall within the scope of the present disclosure.

Use of the reference data may be explained in the following examples. In one example, because occupant data points showing discomfort may vary from occupant-to-occupant, the reference occupant data may indicate that a perspiration increase of thirty percent indicates discomfort for occupant A but no discomfort for occupant B. As such, a vehicle operation command may be provided when this situation is detected in vehicle 100 for occupant A but not for occupant B. In another example, processing circuit 150 may compare occupant data acquired during manual driving mode against occupant data acquired during robotic driving mode (e.g., the reference occupant data) for a predefined period of operation of vehicle 100. For example, the vehicle is turned on in manual driving mode and occupant monitoring system 130 begins acquiring occupant data specific to manual driving mode. Robotic driving mode is then activated and occupant monitoring system 130 acquires occupant data during this mode. Processing circuit 150 utilizes the manual driving mode occupant data as a reference for the robotic driving mode occupant data. Each time the vehicle is turned off, new reference data may be required (in other embodiments, the reference data may be stored from one operating instance to a subsequent instance). In this embodiment, vehicle 100 may need to be operated in manual driving mode for a predetermined amount of time prior to sufficient reference occupant data being acquired. For example, three minutes of operation may be insufficient.

Processing circuit 150 may also determine which vehicle operation command to provide based on a comparison of the acquired occupant data to a stored profile of a vehicle occupant. In one embodiment, processing circuit 150 identifies a vehicle occupant and then retrieves an occupant profile for the identified occupant (e.g., from memory device 154). Identification may be based on facial recognition, an identifying input from the occupant via input/output device 110, etc. The occupant profile includes occupant-specific information. Occupant-specific information may be provided via input/output device 110 and include health information of an occupant (e.g., a tobacco user, history of heart problems, etc.), age, gender, and preferences (e.g., vehicle operating parameters that the occupant is comfortable with as opposed to uncomfortable with). Processing circuit 150 may utilize the occupant-specific information to determine a discomfort level of that occupant during the robotic driving mode. Thus, the occupant profile may represent the reference occupant data for the specific occupant. As an example, a doctor may have prescribed the occupant to keep his or her heart rate below ninety beats-per-minute. When and if occupant monitoring system 130 detects that person to have a heart rate at or above ninety beats-per-minute, processing circuit 150 provides an output to check on the person. In some embodiments, processing circuit 150 provides a vehicle operation command to adjust the vehicle operating parameter that caused or may have caused the increased heart rate (e.g., increase the following distance to more than twenty feet because the increased heart rate is detected whenever the following distance decreases below fifteen feet).

According to one embodiment, identification may be via a recognition by processing circuit 150 of personal electronic device 160. As shown, processing circuit 150 is communicably coupled to personal electronic device 160. As described above, processing circuit 150 may communicate with the components of FIG. 1 in either one or both of wired and wireless protocols (e.g., Wi-Fi, USB, Bluetooth, Internet, CAN, WLAN, etc.). Accordingly, personal electronic device 160 may communicate with processing circuit 150 via one or more of wired and wireless protocols. For example, vehicle 100 may include a USB charging port for a smartphone (i.e., personal electronic device 160). An occupant may insert the smart phone on the USB charging port to establish a communication link between processing circuit 150 and the smartphone. Input/output device 110 (e.g., a touchscreen, etc.) may then indicate that the smartphone is connected. In another example, personal electronic device 160 may utilize Bluetooth pairing to communicably couple to processing circuit 150. In still another example, identification by processing circuit 150 may via an identification of an IP address for each specific personal electronic device 160. In each case, upon recognition or identification, a corresponding occupant profile may be retrieved (e.g., stored in memory device 154) that represents the reference occupant data for the identified occupant.

In some embodiments, upon recognition, processing circuit 150 may provide one or more confirmation commands to input/output device 110. For example, a graphical image may appear on a touchscreen that states "Welcome back, John. Please enter your personal identification number (PIN) to confirm your identity." The operator of the device may either enter the correct PIN, incorrect PIN, or (in some embodiments) bypass the confirmation screen to acquire occupant data without occupant profile retrieval. If the correct PIN is received, processing circuit 150 retrieves the corresponding occupant profile. If an incorrect PIN is received more than a predefined number of times (e.g., five, etc.), a security alert may be provided by processing circuit 150 (e.g., send a signal to a remote monitoring service to alert them of a possible stolen item, sound an alarm, etc.). Particular response protocol may be prescribed via input/output device 110. While the aforementioned example is described in regard to a PIN, it should be understood that many other types of confirmation codes or inputs may be used (e.g., facial recognition, voice recognition, pupil recognition, fingerprint scanner, etc.), with all such variations intended to fall within the scope of the present disclosure.

Processing circuit 150 may also provide a vehicle operation command based on both the occupant data and the vehicle operation data. More particularly, the vehicle operation command may be based on both the occupant data and a vehicle operating parameter, as indicated by the vehicle operation data. Thus, the vehicle operation command may be tailored to the vehicle operating parameter that caused or likely caused the discomfort in one or more occupants. For example, during robotic driving mode, the occupant data indicates an average audible characteristic of no gasps or heavy breathing for the occupants of the vehicle. However, whenever the vehicle is brought to a stop, occupant monitoring system 130 detects a gasp or sudden intake of breath. Processing circuit 150 may determine that one or more occupants experience discomfort during stopping. Accordingly, processing circuit 150 may command that the stopping distance for the vehicle be increased, such that the vehicle employs a more gradual stop.

In addition to determining and providing vehicle operation commands, processing circuit 150 may also generate one or more outputs based on the occupant data and the vehicle operation data. The output may be provided via input/output device 130. The output may include the occupant data (e.g., a current pulse rate), a determined or estimated level of discomfort, one or more proposed vehicle operation commands, correlations between the occupant data and one or more vehicle operating parameters, etc. Based on the output, an occupant may provide a response. The response may include an acceptance, rejection, or modification to a proposed vehicle operation command; a replacement vehicle operation command; an actual level of discomfort; etc. Accordingly, the output allows the occupant(s) to monitor and provide inputs regarding the provided by processing circuit 150.

Defining these operating conditions of processing circuit 150 may be via input/output device 110. Accordingly, input/output device 110 may include a graphical user interface, such as a touchscreen, a voice interface, a keyboard interface, and/or any other interface capable of allowing communications between a user or occupant of vehicle 100 and processing circuit 150. Through input/output device 110, users may define when occupant data is gathered (e.g., only during robotic driving mode), what vehicle operation commands are permitted (e.g., processing circuit 150 must receive an instruction from the occupant via the device 110 prior to transmitting a command), acceptable operating ranges for one or more occupant data points, occupant-specific information, etc.

Figure 2:
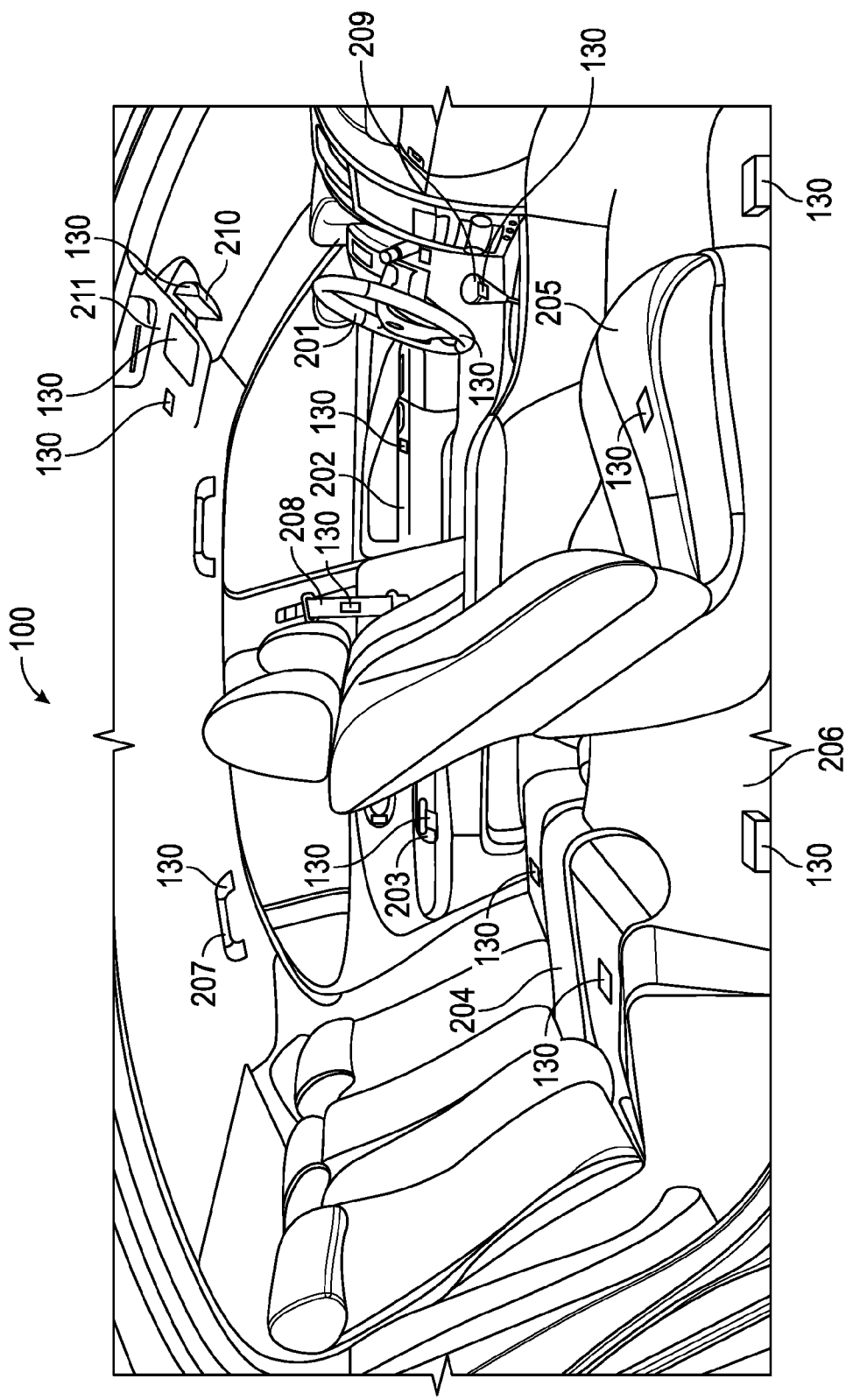
FIG. 2 is a diagram of sensor locations for an occupant monitoring system in a vehicle, according to one embodiment.
Figure 3:
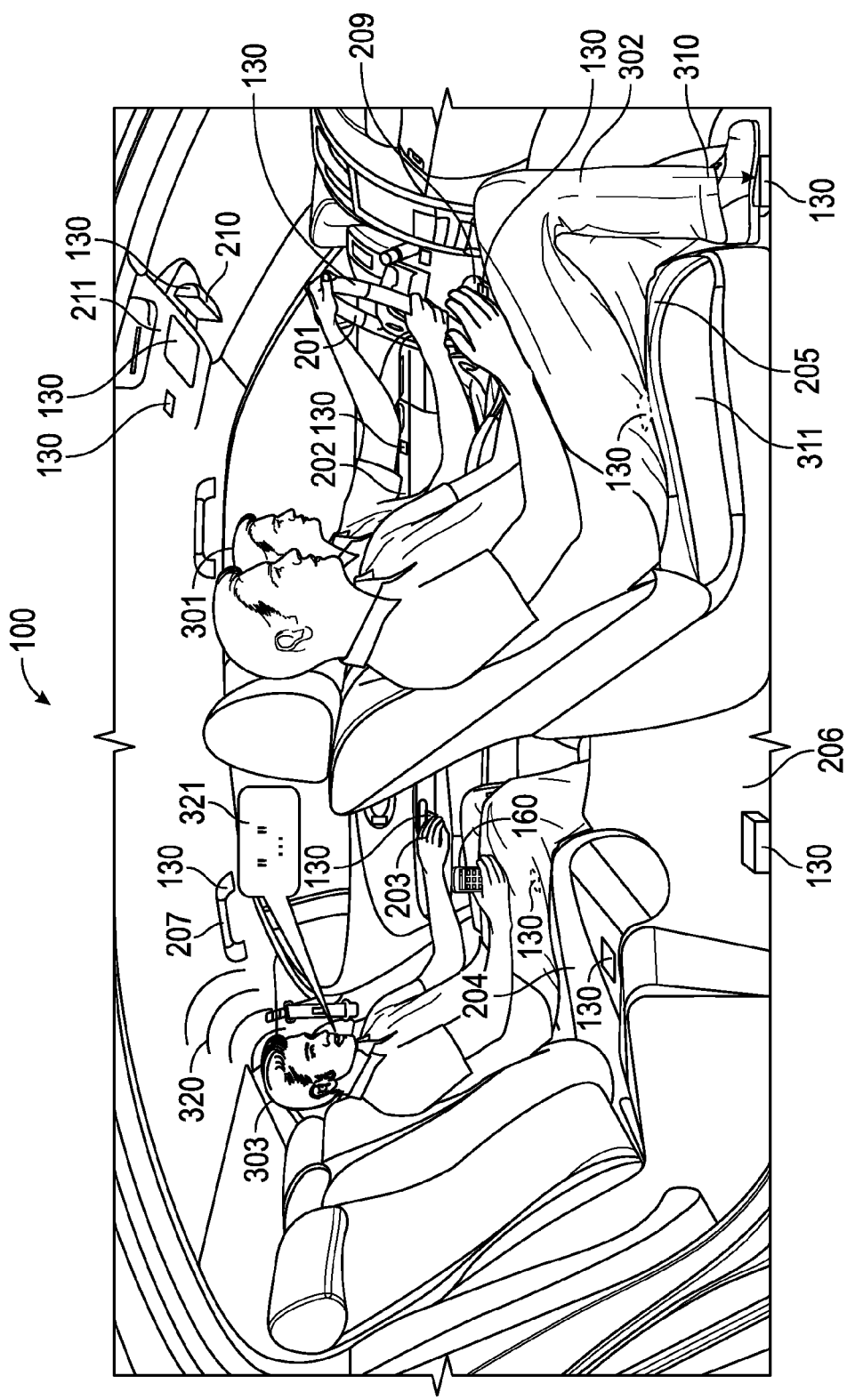
FIG. 3 is a diagram of an occupant monitoring system acquiring occupant data from occupants in a vehicle, according to one embodiment.
Figure 4:
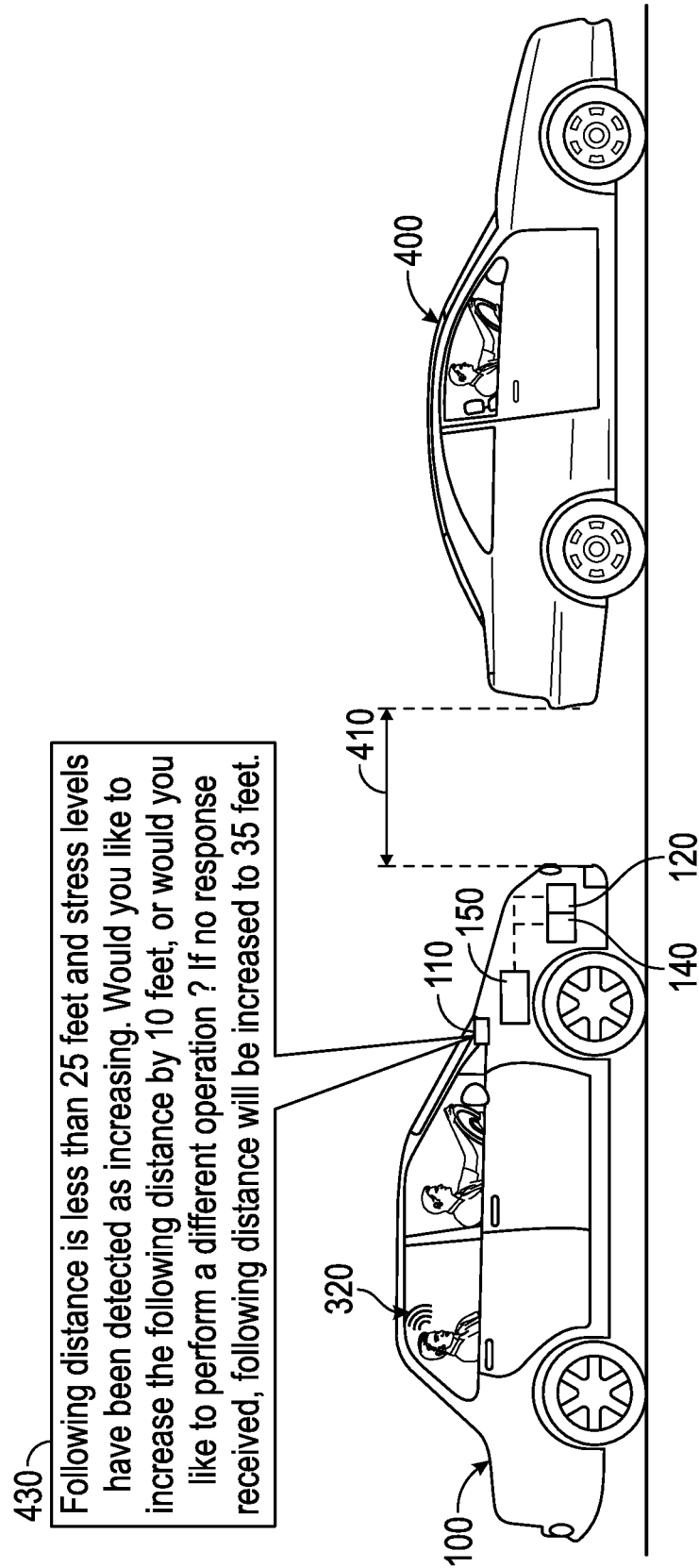
FIG. 4 is a diagram of a vehicle with an occupant monitoring system responding to a situation that caused discomfort for an occupant of the vehicle, according to one embodiment.

Referring now to FIGS. 2-4, an example operation of vehicle 100 with occupant monitoring system 130 and processing circuit 150 is shown according to one embodiment. FIG. 2 depicts a configuration of sensor locations for the occupant monitoring system 130 in vehicle 100. The sensors are generically labeled by reference numeral 130 because they may be embodied as physiological response sensors 132, physical response sensors 134, acoustic sensors 136, and any other sensor type or combination of multiple types of sensors. Thus, as shown, occupant monitoring system 130 sensors may be placed on steering wheel 201, driver side armrest 202, rear seat passenger armrest 203, rear seats 204, front passenger seat 205, floor 206, overhead handle 207, seatbelts 208, transmission shifter 209, rearview mirror 210, and ceiling 211. These locations represent example sensor locations, such that many other positions are possible.

In this embodiment, when vehicle 100 is turned on, occupant monitoring system 130 begins to acquire occupant data (e.g., manual driving mode data) regarding occupant 301, occupant 302, and occupant 303 (FIG. 3). Prior to activation of the robotic driving system, sensor 130 of seat 205 is monitoring force 311 from occupant 302. Sensor 130 of floor 206 is monitoring foot force 310 from occupant 302. Occupant 303 is emitting a physiological response 320 and muttering speech 321. This manual driving mode data may be utilized as reference data for processing circuit 150 (described above). After initiation of robotic driving system 148 of vehicle systems 140, the occupant data is reacquired. Processing circuit 150 compares the occupant data acquired during the robotic driving mode to the occupant data acquired during the manual driving mode. As described above, processing circuit 150 may determine one or more vehicle operation commands if the occupant data acquired during the robotic driving mode differs more than an acceptable amount from the occupant data acquired during the manual driving mode.

As also mentioned above, processing circuit 150 may determine a vehicle operation command based on the vehicle maneuver that caused the likely discomfort. For example, FIG. 4 shows vehicle 100 at following distance 410 from vehicle 400. If the following distance for robotic driving mode is set at twenty-five feet and vehicle 100 is less than twenty-five feet to vehicle 100, processing circuit 150 may ask the occupant(s) if they are comfortable via input/output device 110 (i.e., output 430). Processing circuit 150 may also provide a proposed vehicle operation command (see output 430 stating "would you like to increase the following distance by ten feet?"). Additionally, if no response is received to the proposed command, processing circuit 150 may indicate the next course of action (see output 430). While processing circuit 150 is described above to provide an audible proposed command, in other commands, processing circuit 150 may communicate with the occupants graphically (e.g., via a touchscreen, etc.,) or any other process. For example, processing circuit 150 may also present a virtual control, e.g., a slider on a touchscreen, allowing a user to adjust one or more parameters that relates to their detected distress. Accordingly, the examples described herein are not meant to be limiting, but broadly interpreted.

Thus, in operation, occupant monitoring system 130 acquires data regarding occupants 301-303. The occupant data indicates a level of discomfort and processing circuit 150 provides output 430 based on this determination. Processing circuit 150 then operates based on a response from the occupants or, if no response, on a predefined operation. In sum, processing circuit 150 via occupant monitoring system 130 is monitoring the occupants to ensure they are comfortable during robotic driving mode and making adjustments if they are not (e.g., one or more vehicle operation commands).

Figure 5:
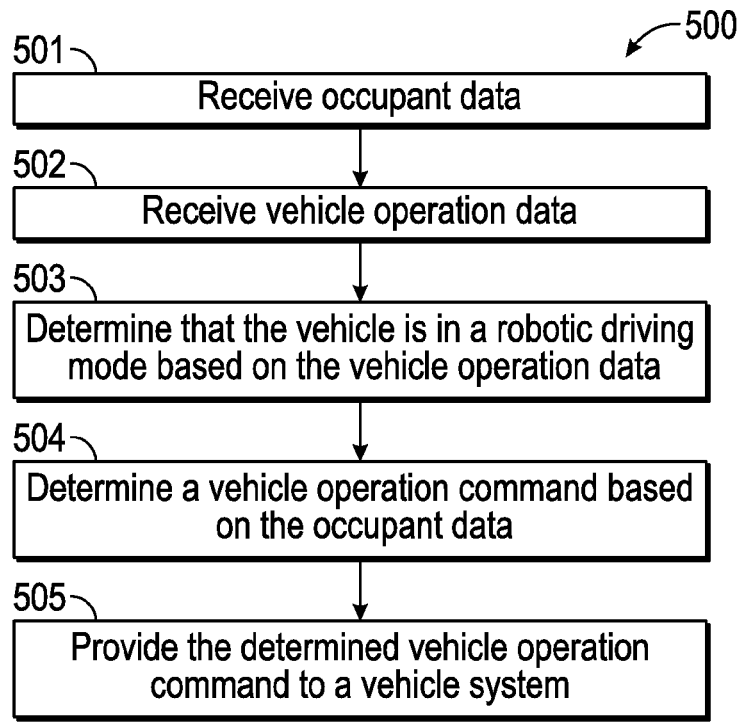
FIG. 5 is a diagram of a method of operating a robotic driving vehicle, according to one embodiment.
Figure 6:
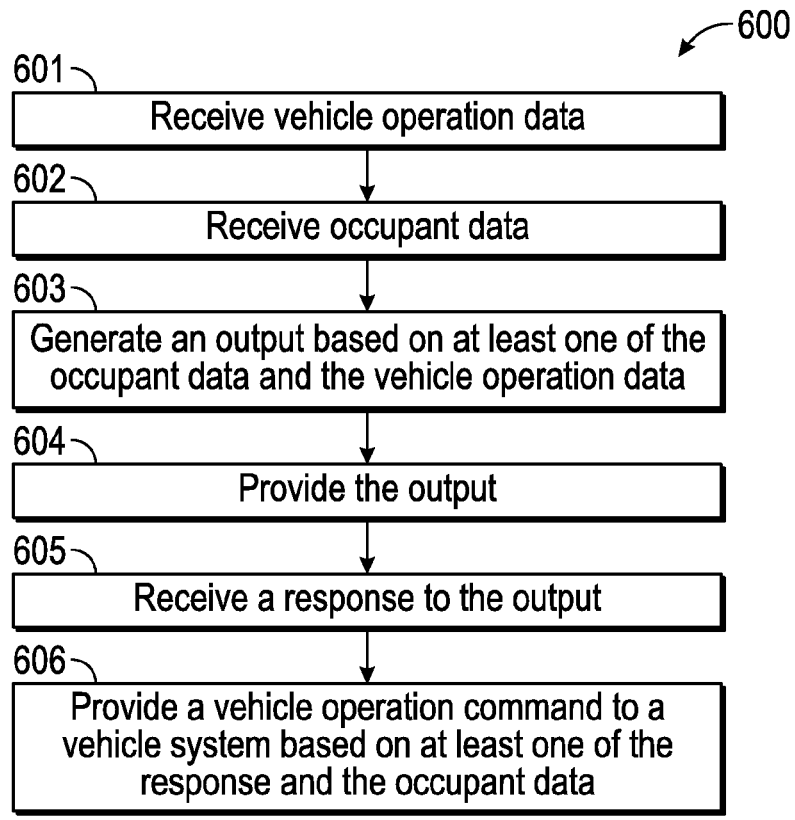
FIG. 6 is another diagram of a method of operating a robotic driving vehicle, according to one embodiment.
Figure 7:
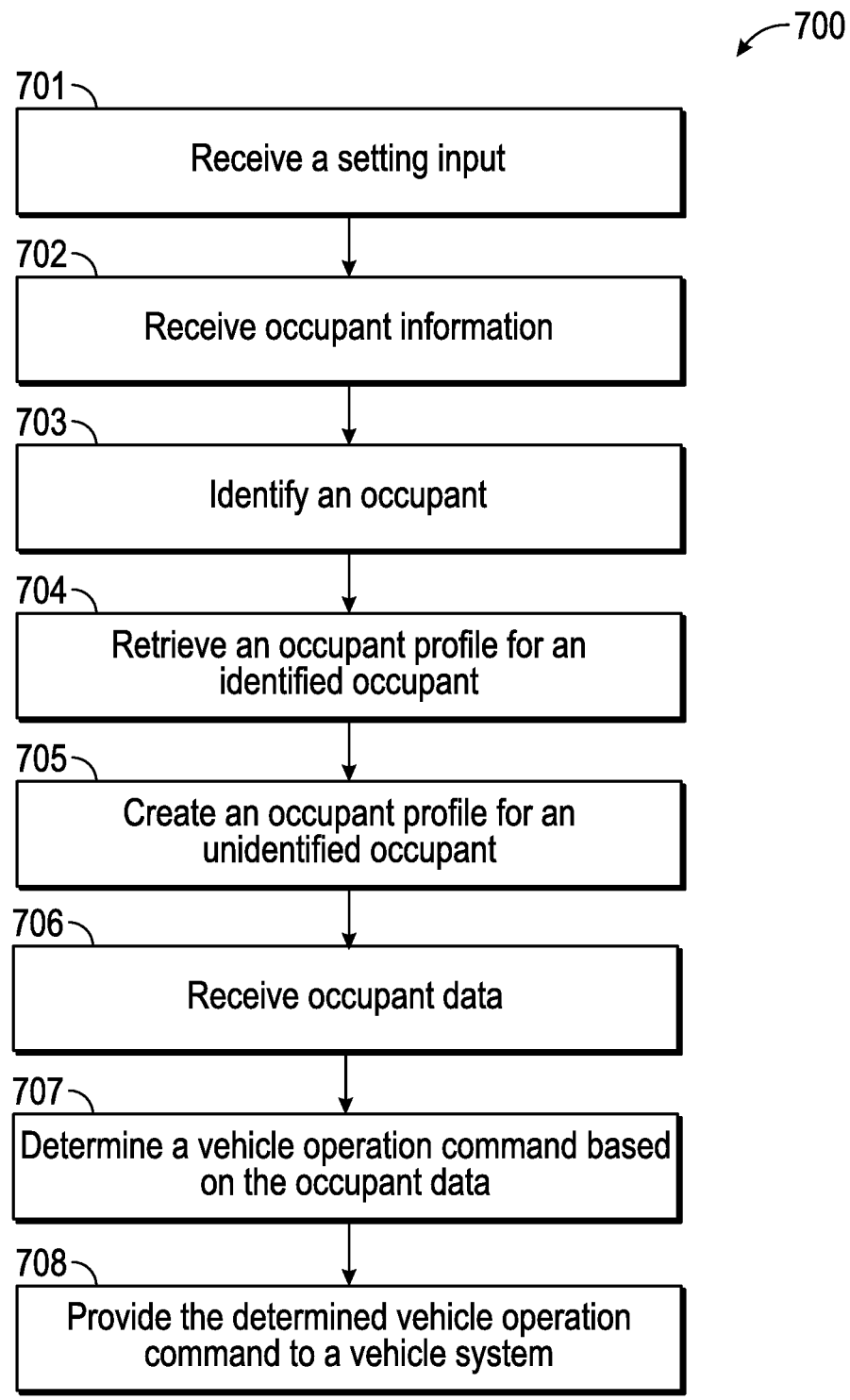
FIG. 7 is another diagram of a method of operating a robotic driving vehicle, according to one embodiment.

Referring now to FIGS. 5-7, methods of operating a robotic driving vehicle are shown according to one embodiment. Methods 500-700 may be utilized with the components of FIG. 1. Accordingly, methods 500-700 are described herein with regard to the components of FIG. 1.

Method 500 represents a method of controlling a robotic driving vehicle based on the comfort of one or more occupants of the vehicle. Method 500 may begin by occupant data being received (501). In one embodiment, the occupant data is received by a processing circuit, such as processing circuit 150. The occupant data provides an indication of discomfort of the occupants (or, in some embodiments, each occupant individually) in vehicle 100 while vehicle 100 is in robotic driving mode. As mentioned above, the occupant data may be acquired by an occupant monitoring system 130 using one or more sensors. Accordingly, the occupant data may include an eye motion, a pupil size, a perspiration amount, a perspiration rate, a temperature, a pulse rate, audible information, an amount of shaking or trembling, an exertion of force (e.g., feet are pressed to floor the instant the vehicle is "self-driving"), or a facial feature (e.g., a frown).

Vehicle operation data is received (502). In one embodiment, processing circuit 150 receives the vehicle operation data. The vehicle operation data provides an indication of one or more vehicle operating parameters as described above. Based on the vehicle operation data, it is determined that the vehicle is a robotic driving mode (503). In one embodiment, processing circuit 150 determines that the vehicle is in a robotic driving mode based on the vehicle operation data (503). Based on the occupant data, a vehicle operation is determined (504) and provided to a vehicle system (505). In one embodiment, processing circuit 150 determines a vehicle operation command (504) and provides the command to a vehicle system (505). The vehicle operation command is structured to affect a vehicle operating parameter of the vehicle while the vehicle is in a robotic driving mode.

As mentioned above, the vehicle operation command may be determined in a wide variety of ways. The determination methodology may be set via input/output device 100. Accordingly, as mentioned above, the determination may be based on: a gradation level of one or more occupant data points from a predefined standard; a plurality of occupant data points, as opposed to just a sole occupant data point; occupant data for a specific occupant, rather than the occupants as a whole; a comparison of one or more occupant data points to one or more reference occupant data points; a comparison of the acquired occupant data to a stored profile of a vehicle occupant; and/or on both the occupant data and the vehicle operation data. Method 500 may be configured to run continuously, such that the discomfort of one or more occupants in the vehicle is minimized over time.

Referring next to FIG. 6, method 600 depicts another embodiment of controlling a robotic driving vehicle. Method 600 may begin by receiving vehicle operation data (601) and occupant data (602). In one embodiment, the vehicle operation data and occupant data is received by processing circuit 150. The vehicle operation data provides an indication of one or more vehicle operating parameters. An output based on either one or both of the occupant data and the vehicle operation data is generated (603). In one embodiment, a processing circuit, such as processing circuit 150, generates the output. The output includes, but is not limited to: the occupant data acquired; a proposed vehicle operation command; a correlation between an occupant data point and a vehicle operating parameter (e.g., during braking, the occupant data points indicate a level of discomfort); the occupant data relative to an occupant profile (see method 700); an average of one or more occupant data points for a particular time frame; a peak level of one or more occupant data points for a particular time frame; an average or peak level of one or more occupant data points for each vehicle occupant individually and/or collectively; an average and/or peak discomfort level based on the occupant data for either a specific occupant or all the occupants for a particular time frame; a proposed vehicle operation command based on the discomfort detected; etc. One or more of the generated outputs may then be provided to an occupant of the vehicle (604).

A response to the output is received (605). In one embodiment, processing circuit 150 receives the response to the output. The response may be structured to control a vehicle operating parameter. Accordingly, the response may include a vehicle operation command, a rejection to a generated vehicle operation command, a modification to a generated vehicle operation command, and an acceptance to a generated vehicle operation command. Processing circuit 150 may also receive an input to select to view or to generate one or more of the outputs above. This input may be received via input/output device 110.

A vehicle operation command is provided to a vehicle system based on at least one of the response, the occupant data alone, and the occupant data in connection with the vehicle operation data (606). In one embodiment, processing circuit 150 provides the vehicle operation command to the vehicle system. When the vehicle operation command is based on the occupant data alone, process 606 may function similar to process 505 of method 505. Utilizing both the occupant data and the vehicle operation data, processing circuit 150 determines what vehicle maneuver (i.e., vehicle operating parameter) caused the characteristic of the occupant data. Accordingly, processing circuit 150 tailors the vehicle operation command to affect those maneuvers in order to alleviate the discomfort that was indicated by the characteristic in the occupant data.

Method 600 enables the occupants to interact with processing circuit 150 prior to a vehicle operation command being provided (e.g., process 605). Further, method 600 allows occupants to examine how processing circuit 150 perceives them to react during in robotic driving mode. Via input/output device 110, the occupants may adjust the determinations made by processing circuit 150 to optimize one or more operations of processing circuit 150.

As an example, occupant A may be unfamiliar with a robotic driving car. The vehicle is initially operated manually (i.e., operator controlled). The occupant monitoring system is acquiring occupant data for each occupant in the vehicle. After the vehicle has been operated for ten minutes, robotic driving mode is initiated. Occupant monitoring system continues to acquire occupant data for each occupant. Processing circuit 150 receives the occupant data and determines a substantial increase in grip strength of a handhold of occupant A relative to that received in manual driving mode. Accordingly, processing circuit 150 may (via input/output device 110) state: "Potential excessive discomfort has been detected for Occupant A. Would you like to deactivate robotic driving mode?" At this point, occupant A may voice their discomfort. Alternatively, occupant A may provide an indication that conditions are acceptable and that continued operation of the vehicle in robotic driving mode is acceptable. After ten additional minutes, processing circuit 150 may check in with occupant A to make sure everything is still acceptable. Alternatively, processing circuit 150 may only check in again if the occupant data indicates another substantial deviation.

If occupant A indicates that they are not comfortable with robotic driving mode, processing circuit 150 may perform a series of operations. If the discomfort was detected immediately upon activation of robotic driving mode, processing circuit 150 may determine that it is the robotic driving that caused the discomfort. Accordingly, processing circuit 150 may completely deactivate robotic driving mode (upon warning to the driver of the vehicle). Alternatively, processing circuit 150 may present one or more vehicle operation commands or receive a vehicle operation command from the uncomfortable occupant A. For example, occupant A may input: "Please drive slower than the speed limit; brake slowly; and take corners gradually." Here, occupant A is defining vehicle operating parameters for the vehicle. Processing circuit 150 may provide these commands to one or more vehicle systems and check in with occupant A after a few minutes (or another predefined time period) to see if they are more comfortable. If occupant A indicates that they are not, additional vehicle operation commands may be provided or an affirmative act to deactivate robotic driving mode may be provided.

Referring now to FIG. 7, a method of using a custom occupant monitoring system is shown according to one embodiment. Method 700 is initiated a setting input being received (701). In one embodiment, processing circuit 150 receives the setting input. The setting input is structured to customize operations of processing circuit 150 and occupant monitoring system 130 in vehicle 100. The setting input may define how often occupant data is acquired. The setting input may define when and what generated output to provide (e.g., processes 603-604 of method 600). The setting input may include one or more predefined standards that indicate discomfort (e.g., forces greater than X on the handholds indicate discomfort, temperature increases more than Y indicate discomfort, etc.). The setting input may further define how a vehicle operation command is determined. For example, acquired occupant data is compared against preset values. In another example, the acquired occupant data is compared against reference occupant data. Further, the setting input may define what vehicle operation command is provided based on the acquired occupant data. For example, while in robotic driving mode, if an occupant's temperature increases above one-hundred degrees, processing circuit 150 may command the air-conditioning system to activate and provide an output asking the occupant if they are comfortable. In another example, if the grip force on a handhold increases in robotic driving mode, processing circuit 150 may command the vehicle to slow down its speed. Thus, a user or occupant has a wide amount of customization possibilities via the setting input.

Moreover, the setting input may also define limits on the vehicle operation command of processes 707-708. For example, in one embodiment, processing circuit 150 operates to alleviate discomfort of one or more occupants in vehicle 100 during robotic driving mode. In an alternate embodiment, processing circuit 150 operates to prevent an abuse or likely abuse of power of the robotic driving vehicle. In this embodiment, the setting input may limit one or more vehicle operation commands. For example, while in robotic driving mode, the occupants keep instructing the vehicle to go faster and faster. However, a prior setting input may have limited vehicle speed to five miles-per-hour greater than the speed limit based on the driving conditions (e.g., traffic permitting). Via a location positioning system, processing circuit 150 is able to obtain speed limit information. Although the occupants keep instructing the vehicle to go faster above the speed limit, processing circuit 150 operates to limit the vehicle speed despite those commands.

In another embodiment, the setting input may instruct processing circuit 150 to work in a somewhat opposite manner. For example, while the vehicle is being operated in a manual driving mode, the occupant data may indicate that none of the occupants appear to be uncomfortable. Accordingly, processing circuit 150 may provide an output asking them whether they would like to activate robotic driving mode. Thus, the setting input (701) is structured to control one or more functions of processing circuit 150.

Occupant information is received (702). In one embodiment, processing circuit 150 receives the occupant information. As mentioned above, the occupant information, or occupant-specific information, may include health information of an occupant (e.g., a tobacco user, history of heart problems, etc.), age, gender, and preferences (e.g., vehicle operating parameters that the occupant is comfortable with as opposed to uncomfortable with). The occupant information may be provided via input/output device 110. The occupant information may also include identity information. For example, processing circuit 150 may store occupant profiles for a variety of occupants and upon entering vehicle 100, occupant A may identify himself/herself (703) such that his/her occupant profile is retrieved. Identification of the occupant may be explicit, as in the example above, or implicit. For example, occupant monitoring system 130 may include a camera that takes a facial picture of an occupant where processing circuit 150 utilizes a facial recognition program to identify the occupant. Thus, occupant identification may be via occupant data acquired. In another example, processing circuit 150 may recognize personal electronic device 160 to identify an occupant. All variations are intended to fall within the scope of the present disclosure.

In still further embodiments, as described above, processing circuit 150 may categorize an occupant upon identification (e.g., a driver). In this case, processing circuit 150 may pay closer attention to higher classified occupants (e.g., provide vehicle operation commands to accommodate their feelings over the feelings of others). Identification of the occupant type may be via an input (e.g., a touchscreen may receive an input that the person is a driver). Identification of the occupant type may be via recognition of personal electronic device 160 (e.g., processing circuit 150 recognizes personal electronic device 160 and retrieves a corresponding occupant profile that indicates the identified person is an owner). Identification of the occupant type may be based on proximity sensors (e.g., Occupant data acquired from an occupant in the driver seat may be classified as occupant data of the driver. Occupant data acquired from passengers in any other seat may be classified as occupant data for a passenger(s).).

Upon identification (process 703), an occupant profile is retrieved for each identified occupant (704). In one embodiment, processing circuit 150 retrieves the occupant profile for each identified occupant. The occupant profile includes the occupant information for that occupant. This information may be based on occupant data acquired over one or more vehicle trips and/or information provided by the occupant. The occupant profile may also include one or more preferences for that occupant. These preferences may include one or more occupant data levels that indicate that the occupant is uncomfortable (in an alternate embodiment, show comfort); preferred vehicle operating parameters (e.g., "I prefer at least twenty-five feet of following distance"); specific vehicle operation commands for specific acquired occupant data points; etc.

If the occupant is not identified or does not have an occupant profile, an occupant profile may be created (705). For example, a new personal electronic device 160 (e.g., not previously coupled to processing circuit 150) may be detected by processing circuit 150 (e.g., via a USB charging port). Processing circuit 150 may automatically create a profile corresponding to the device, such that while the identity of the occupant owning/operating the device 160 is unknown, processing circuit 150 recognizes the device. In one example, the occupant operating the device may provide an identifying input via input/output device 110 (e.g., a touchscreen). The input may provide an identification of that occupant's relative location in the vehicle, such that the occupant data acquired from that location corresponds with the personal electronic device 160 (and, the self-identified occupant). In another example, because the device is likely plugged into a center console or other location that may not correspond with a location of owner/operator of the device, processing circuit 150 may use an elimination-type algorithm, process, or estimation to determine a location of the occupant that corresponds to the device. For example, based on inputs of other occupants in the vehicle, processing circuit 150 may determine that device 160 belongs to the remaining, unidentified occupant. Further, processing circuit 150 may determine the location of each personal electronic device 160 in vehicle 100 based on at least one of a signal strength indicator (e.g., received signal strength identification, etc.), other signal original techniques/methods, another sensor in the vehicle identifying the location of each particular device, and any other location identifying procedure for personal electronic device 160. Based on the determined location or relative locations of personal electronic device in the vehicle, processing circuit 150 may determine which occupant owns/operates which electronic device (e.g., the device in proximate location to the occupant may be presumed to be owned/operated by that occupant, etc.).

In one embodiment, processing circuit 150 may create the occupant profile. However, if the occupant does not wish to create a profile, processing circuit 150 may utilize one or predefined standards to gauge that occupant's comfort level during the robotic driving mode. For example, when an occupant's profile is not available to use as a reference, a transient force of X pounds or more on the occupant's seat indicates possible discomfort. In another example, the comparison may be based on that occupant's data (e.g., the force on the seat) prior to activation of robotic driving mode. If there is an increase of more than ten percent, processing circuit 150 may determine that the occupant is not comfortable and provide one or more outputs (e.g., "would you like the vehicle to slow down?", "would you like to deactivate robotic driving mode?", etc.).

In another embodiment, the occupant profile may be transferable between devices (e.g., computing devices such as a computer, tablet, or a smartphone) and vehicles. For example, the occupant profile may be stored in a cloud networking environment or another environment (e.g., a website). In this case, data may be uploaded from the vehicle to the cloud, or a website maintaining the profile, or to a user's device (e.g., phone, USB drive, etc.), etc. In this situation, the data may later be transferred to another vehicle for use or to a non-vehicle computer (e.g., the user has a program on their phone or home computer allowing them to adjust their preferences or other data). In an alternate embodiment, the user may interact with a processing circuit of the vehicle to make these adjustments. All such variations are intended to fall within the spirit and scope of the present disclosure.

Occupant data is received (706). In one embodiment, processing circuit 150 receives the occupant data. Based on the occupant data, one or more vehicle operation commands are determined (707), which are then provided to a vehicle system (708). In one embodiment, processing circuit 150 determines the vehicle operation commands and provides them to the vehicle system. As mentioned above, the determination of what commands to provide may be based on the setting input. Moreover, the determination may be based on the occupants profile relative to the received occupant data. For occupants without profiles, the determination may be based on predefined standards that may be defined via the input setting. Thus, method 700 provides for a customization of the operations of processing circuit 150 with monitoring system 130.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A vehicle, comprising:
    an occupant monitoring system configured to acquire occupant data regarding an occupant of the vehicle; and
    a processing circuit coupled to the occupant monitoring system, the processing circuit configured to:
        receive the occupant data and an occupant type regarding the occupant, wherein the occupant type includes one of a driver and a passenger;
        determine a vehicle operation command based on the occupant data and the occupant type, the vehicle operation command configured to affect operation of the vehicle while the vehicle is in a robotic driving mode; and provide the vehicle operation command to a vehicle system.

2. The vehicle of claim 1, wherein the occupant data provides an indication of discomfort of an occupant in the vehicle while the vehicle is in the robotic driving mode.

3. The vehicle of claim 1, wherein the occupant data includes at least one of an eye motion, a pupil size, a perspiration amount, a perspiration rate, a temperature, a pulse rate, audible information, an amount of shaking, an exertion of force, and a facial feature.

4. The vehicle of claim 1, wherein the vehicle command determination is based on an occupant data point being outside a predefined standard.

5. The vehicle of claim 4, wherein the predefined standard includes at least one of an acceptable operating range and a threshold level, the threshold level defining at least one of a minimum level and a maximum level for one or more occupant data points.

6. The vehicle of claim 1, wherein the vehicle command determination is based on a gradation level of an occupant data point relative to a predefined standard.

7. The vehicle of claim 6, wherein each gradation level corresponds with a different vehicle operation command.

8. The vehicle of claim 1, wherein the vehicle command determination is based on occupant data for only one occupant of a group of occupants in the vehicle.

9. The vehicle of claim 1, wherein the vehicle command determination is based on a comparison of one or more occupant data points to one or more reference occupant data points included in reference occupant data.

10. The vehicle of claim 9, wherein the reference occupant data represents at least one of an average, a trend, a median value, and a normal operating range for one or more occupant data points.

11. The vehicle of claim 9, wherein the reference occupant data is specific to an occupant that is acquired via one or more vehicle trips.

12. The vehicle of claim 9, wherein the reference occupant data is based on occupant data that is acquired for all occupants in the vehicle during one vehicle trip.

13. The vehicle of claim 9, wherein the reference occupant data is based on occupant data that is acquired for one or more vehicle occupants during a manual driving mode of the vehicle.

14. The vehicle of claim 9, wherein the reference occupant data is based on occupant data that is acquired after a predetermined time of operation of the vehicle.

15. A vehicle, comprising:
an occupant monitoring system configured to acquire occupant data regarding an occupant of the vehicle;
a vehicle monitoring system configured to acquire vehicle operation data; and
a processing circuit configured to:
receive the occupant data and an occupant type regarding the occupant, wherein the occupant type includes one of a driver and a passenger;
receive the vehicle operation data;
provide an output to the occupant regarding operation of the vehicle; and
provide a vehicle operation command to a robotic driving system based on the occupant data, the occupant type, and the vehicle operation data, wherein the vehicle operation command is configured to affect operation of the vehicle while the vehicle is in a robotic driving mode.

16. The vehicle of claim 15, wherein the vehicle operation command is configured to adjust a vehicle operating parameter that caused the occupant data to indicate an occupant discomfort.

17. The vehicle of claim 15, wherein the output includes at least one of the occupant data acquired, a proposed vehicle operation command, and a correlation between an occupant data point and a vehicle operating parameter.

18. The vehicle of claim 15, wherein the processing circuit is configured to receive a response to the provided output, wherein the response includes at least one of a vehicle operation command, a rejection to a generated vehicle operation command, a modification to a generated vehicle operation command, and an acceptance to a generated vehicle operation command.

19. The vehicle of claim 15, wherein the occupant monitoring system includes a sensor configured to acquire the occupant data, wherein the sensor includes at least one of a contacting sensor and a non-contacting sensor.

20. The vehicle of claim 19, wherein the sensor includes a pressure sensor, a microphone, a heart rate/pulse sensor, a moisture sensor, a temperature sensor, and a facial sensor.

21. The vehicle of claim 19, wherein the sensor includes at least one of a physiological response sensor, a physical response sensor, and an acoustic sensor.

22. The vehicle of claim 21, wherein the physical response sensor acquires a physical force generated by an occupant of the vehicle.

23. The vehicle of claim 21, wherein the acoustic sensor acquires at least one of a voluntary sound and an involuntary sound emitted by an occupant of the vehicle.

24. A vehicle, comprising:
an occupant monitoring system configured to acquire occupant data regarding an occupant of the vehicle; and
a processing circuit configured to:
identify the occupant of the vehicle including an occupant type, wherein the occupant type includes one of a driver and a passenger;
retrieve an occupant profile for the occupant based on identification of the occupant;
receive the occupant data;
determine a vehicle operation command based on the occupant data, the occupant type, and the occupant profile, wherein the vehicle operation command is configured to affect operation of the vehicle while the vehicle is in a robotic driving mode; and
provide the vehicle operation command to a vehicle system.

25. The vehicle of claim 24, wherein the vehicle system includes a robotic driving system, wherein the robotic driving system is configured to provide robotic control of the vehicle while the vehicle is in the robotic driving mode.

26. The vehicle of claim 24, wherein identification is based on a personal electronic device of the occupant, wherein the processing circuit is configured to identify the occupant based on recognition of the personal electronic device.

27. The vehicle of claim 24, wherein the processing circuit is configured to weight occupant data corresponding to higher classified occupants types more heavily than occupant data corresponding to lower classified occupant types, and wherein the driver occupant type is a relatively higher classified occupant type than the passenger occupant type.

28. The vehicle of claim 24, wherein the processing circuit is configured to provide a privilege to higher classified occupant types, wherein the privilege includes at least one of an ability to override provided vehicle operation commands, an ability to ignore occupant data from one or more other occupants in the vehicle, and an ability to weight more heavily occupant data from one or more other occupants in the vehicle despite the one or more other occupants being classified in a relatively lower occupant type.

29. The vehicle of claim 24, wherein the occupant data provides an indication of discomfort of the occupant while the vehicle is in the robotic driving mode.

30. The vehicle of claim 24, wherein the occupant profile includes occupant information, the occupant information including at least one of an age, a gender, a piece of health information, and a preference of the occupant.

31. The vehicle of claim 30, wherein the preference includes one or more occupant data levels that indicate a discomfort feeling in the occupant.

32. The vehicle of claim 30, wherein the preference includes a vehicle operation command for various acquired occupant data points.

33. The vehicle of claim 24, wherein the determination is based on one or more occupant data points being outside a predefined standard for one or more occupant data points in the occupant profile.

34. The vehicle of claim 24, wherein the determination is based on a gradation level of an occupant data point relative to a predefined standard of the occupant data point in the occupant profile, wherein each gradation level corresponds with a different vehicle operation command.

* * * * *